(12) United States Patent
Frasch et al.

(10) Patent No.: US 8,076,079 B2
(45) Date of Patent: Dec. 13, 2011

(54) SINGLE MOLECULE DETECTION USING MOLECULAR MOTORS

(75) Inventors: Wayne Frasch, Phoenix, AZ (US); Lyian He, Chandler, AZ (US)

(73) Assignee: Arizona Board of Regents, a body coporate acting for and on behalf of Arizona State University, Scottsdale, AZ (US)

( * ) Notice: Subject to any disclaimer, the term of this patent is extended or adjusted under 35 U.S.C. 154(b) by 290 days.

(21) Appl. No.: 10/582,820

(22) PCT Filed: Dec. 17, 2004

(86) PCT No.: PCT/US2004/042358
§ 371 (c)(1),
(2), (4) Date: Oct. 8, 2008

(87) PCT Pub. No.: WO2005/080603
PCT Pub. Date: Sep. 1, 2005

(65) Prior Publication Data
US 2009/0035751 A1 Feb. 5, 2009

Related U.S. Application Data

(60) Provisional application No. 60/530,547, filed on Dec. 17, 2003.

(51) Int. Cl.
*C12Q 1/68* (2006.01)
*C12M 1/34* (2006.01)
*C07H 21/04* (2006.01)
*C07H 21/02* (2006.01)

(52) U.S. Cl. .................. 435/6.11; 435/287.2; 536/23.1; 536/24.3; 536/25.32

(58) Field of Classification Search .................. None
See application file for complete search history.

(56) References Cited

U.S. PATENT DOCUMENTS
2003/0215844 A1* 11/2003 Chapsky et al. .................. 435/6

FOREIGN PATENT DOCUMENTS
WO WO-2004/053501 A2 6/2004

OTHER PUBLICATIONS

Junge, W., et al., "ATP synthase: an electrochemical transducer with rotatory mechanics," TIBS Trends in Biochemical Sciences, Nov. 1997, 22(11):420-423.

* cited by examiner

*Primary Examiner* — Bradley L Sisson
(74) *Attorney, Agent, or Firm* — Citadel Patent Law; George A. Leone

(57) ABSTRACT

The present invention provides methods and compositions for highly sensitive nucleic acid detection, down to the single nucleic acid molecule level. In one aspect, the present invention provides methods for detecting a target nucleic acid comprising: (a) providing first and second target-specific nucleic acids, wherein the first and second target-specific nucleic acids each comprise sequences complementary to the target nucleic acid; wherein the first target specific nucleic acid is bound to a first affinity tag and the second target-specific nucleic acid is bound to a second affinity tag, wherein the first affinity tag is capable of binding to a molecular motor, and wherein the second affinity tag is capable of binding to a detection probe; (b) contacting the first and second target-specific nucleic acids to a sample under conditions whereby the first and second target-specific nucleic acids will hybridize to the target nucleic acid if the target nucleic acid is present in the sample, wherein upon hybridization to the target nucleic acid the first and second target-specific nucleic acids are directly adjacent to each other; (c) ligating the first and second target-specific nucleic acids together; (d) binding the molecular motor t~ the first affinity tag and the detection probe to the second affinity tag; (e) inducing movement of the molecular motor; and (f) detecting movement of the molecular motor through the detection probe, wherein the movement of the molecular motor serves to detect the target nucleic acid in the sample.

10 Claims, 6 Drawing Sheets

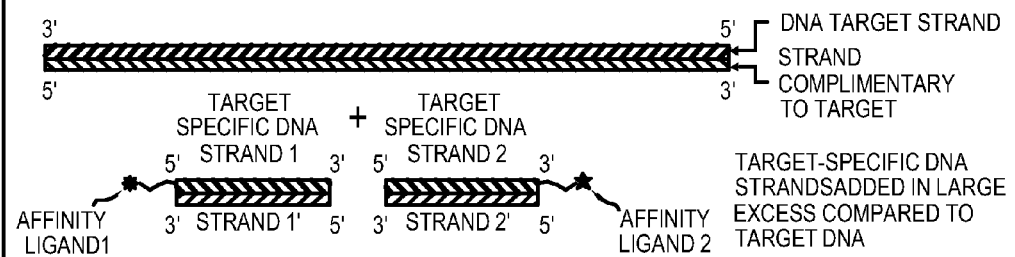
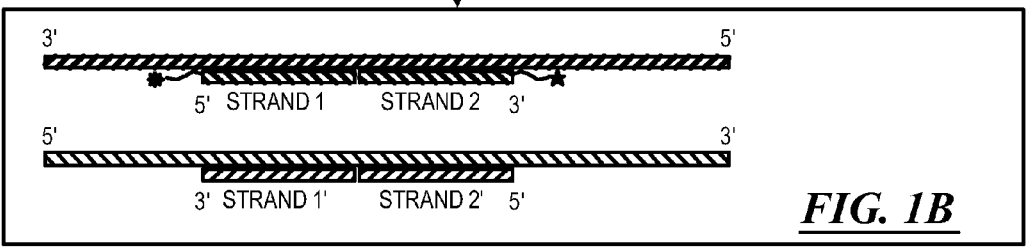
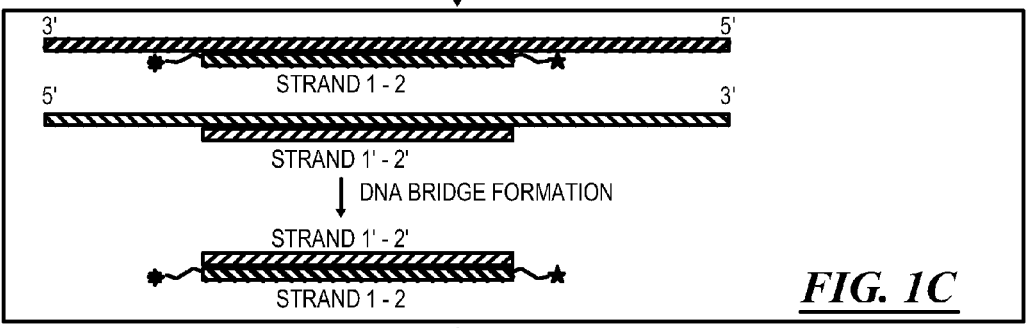
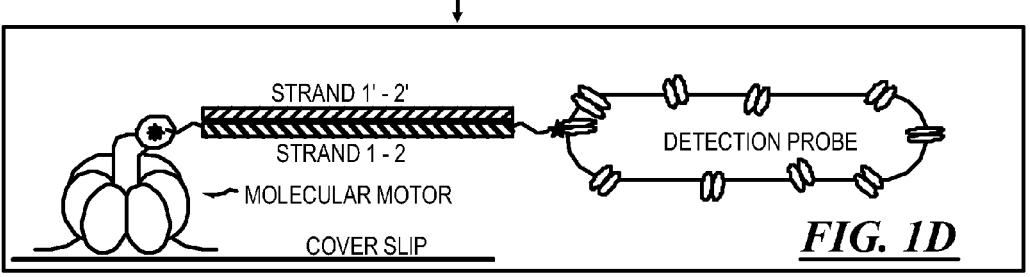

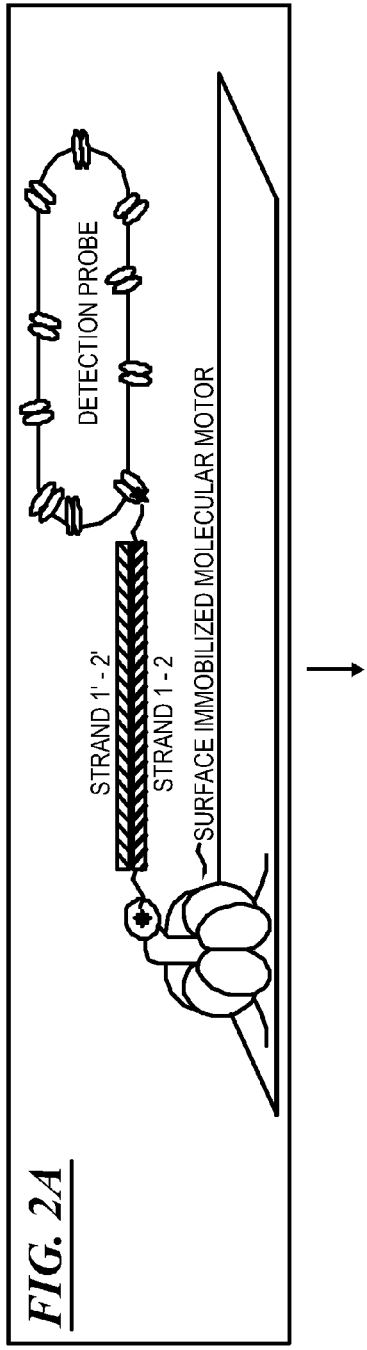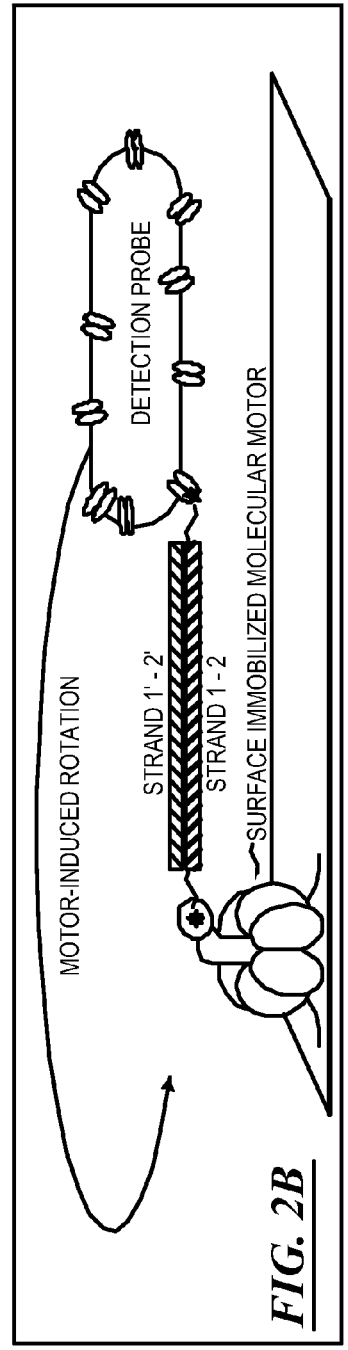

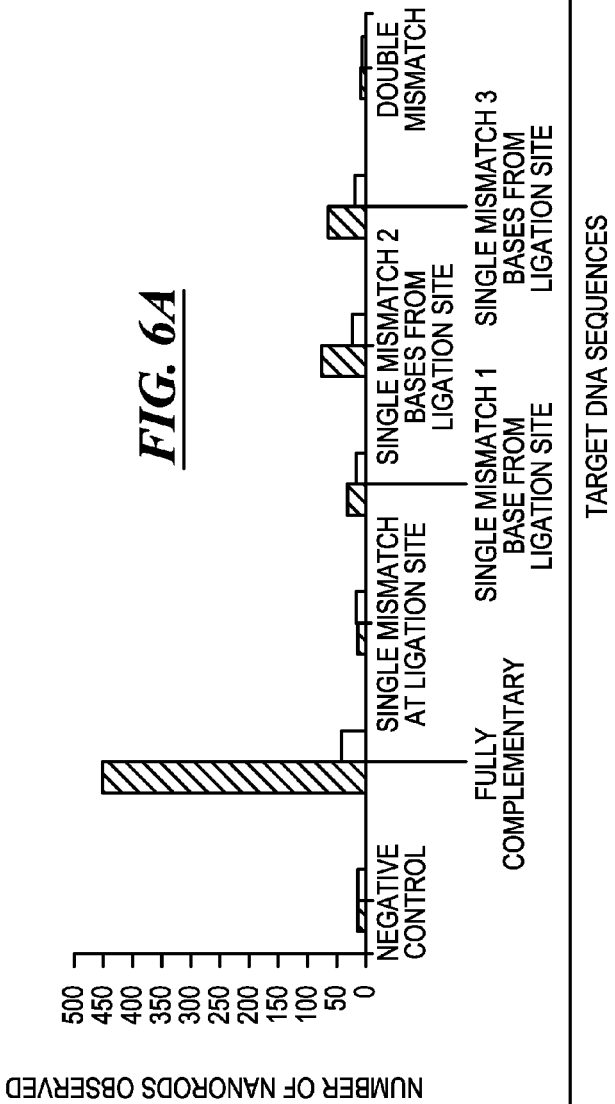

SINGLE MOLECULE DETECTION USING MOLECULAR MOTORS

CROSS REFERENCE

This application claims priority to U.S. Provisional Patent Application Ser. No. 60/530,547 filed Dec. 17, 2003.

STATEMENT OF GOVERNMENT INTEREST

Financial assistance for this project was provided by U.S. Government, DARPA #N66001-03-C-XXXX; thus the United States Government may have certain rights to this invention.

BACKGROUND OF THE INVENTION

Various DNA hybridization methods have been developed in attempts to improve the sensitivity of nucleic acid detection techniques (See, for example, Singh-Zochhi et al., 2003; Castro et al., 1995, 1997, 2000). These methods have shown great potential for ultra-sensitive detection of nucleic acid. However they inherited the intrinsic limitation of DNA hybridization assays such as nonspecific binding, hybridization kinetics, and the requirement for a purified sample. Thus, novel methods of sensitive DNA detection are needed.

SUMMARY OF THE INVENTION

The present invention provides methods and compositions for highly sensitive nucleic acid detection, down to the single nucleic acid molecule level. In one aspect, the present invention provides methods for detecting a target nucleic acid comprising:

(a) providing first and second target-specific nucleic acids, wherein the first and second target-specific nucleic acids each comprise sequences complementary to the target nucleic acid; wherein the first target specific nucleic acid is bound to a first affinity tag and the second target-specific nucleic acid is bound to a second affinity tag, wherein the first affinity tag is capable of binding to a molecular motor, and wherein the second affinity tag is capable of binding to a detection probe;

(b) contacting the first and second target-specific nucleic acids to a sample under conditions whereby the first and second target-specific nucleic acids will hybridize to the target nucleic acid if the target nucleic acid is present in the sample, wherein upon hybridization to the target nucleic acid the first and second target-specific nucleic acids are directly adjacent to each other;

(c) ligating the first and second target-specific nucleic acids together;

(d) binding the molecular motor to the first affinity tag and the detection probe to the second affinity tag;

(e) inducing movement of the molecular motor; and (f) detecting movement of the molecular motor through the detection probe, wherein the movement of the molecular motor serves to detect the target nucleic acid in the sample.

BRIEF DESCRIPTION OF THE FIGURES

FIGS. 1A-D depict assembly of the molecular semaphore of the invention.

FIGS. 2A-B depict rotation of the molecular semaphore of the invention.

FIG. 6A and FIG. 6B provide a summary of experimental results regarding DNA sequence specificity.

DETAILED DESCRIPTION OF THE INVENTION

Figure 3:
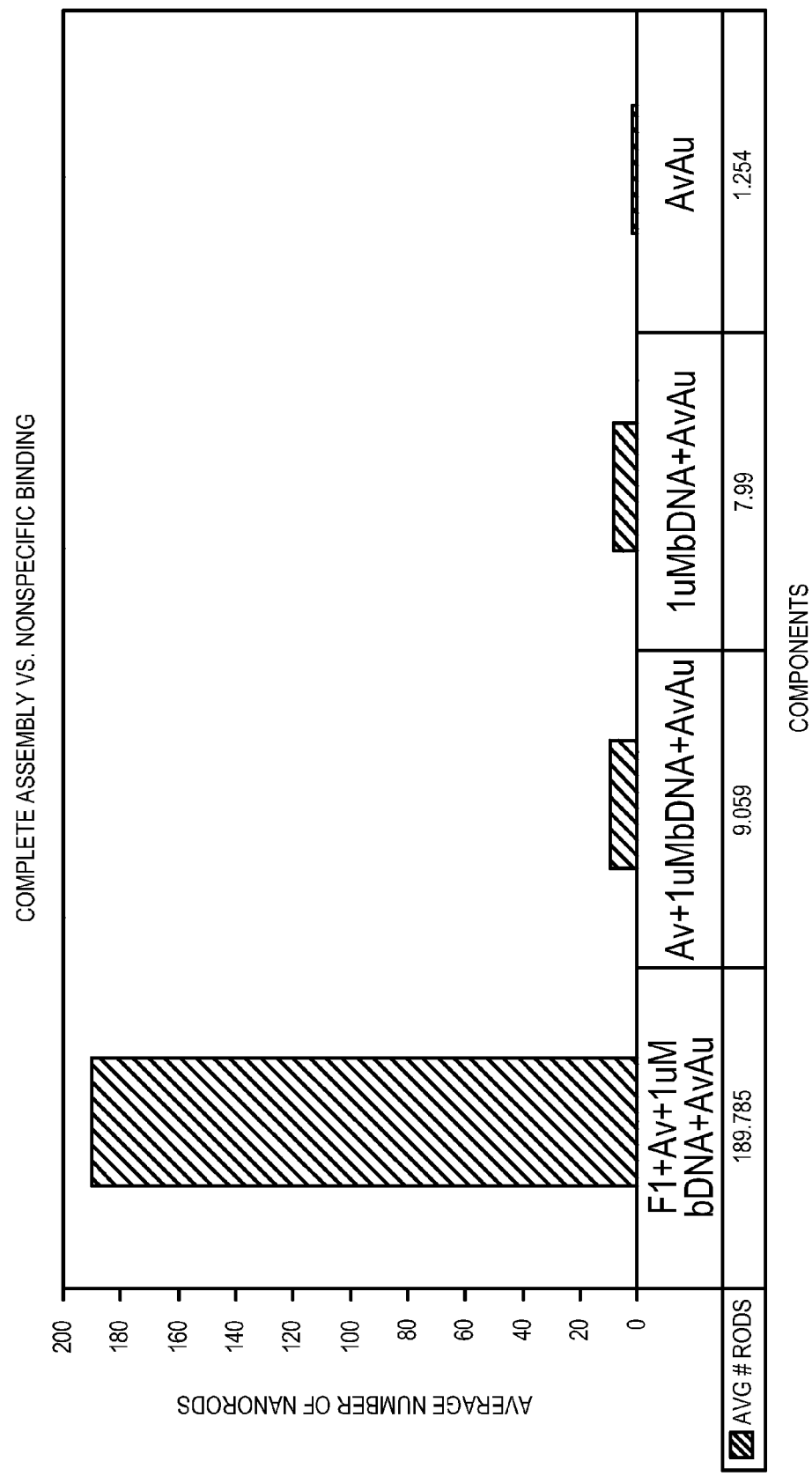
FIG. 3 provides a summary of experimental results regarding complete assembly vs. nonspecific binding.

The present invention provides novel devices and methods for using such devices for extremely sensitive detection of target nucleic acid sequences in a sample. The methods disclosed herein detect a DNA target as the result of ligation with two target-specific nucleic acids, which are ligated only in the presence of the nucleic acid target. The thus-ligated product (also referred to herein as a "Nucleic Acid bridge" or "DNA bridge") is used to bridge a molecular motor and a detection probe (the assembled product which is also referred to herein as a "molecular semaphore."). The detection probe reveals the motion imparted by the molecular motor to the bridging ligated product that is indicative of the nucleic acid target. The observable motion imparted to the probe is observed by an appropriately chosen means of detection of signal from the detection probe. The methods of the invention are capable of detecting single molecules of the target nucleic acid, and thus provide an extremely sensitive technique for target detection that is of wide applicability, including but not limited to clinical diagnostics, forensic analysis, gene expression analysis, DNA sequencing, and DNA computing.

Thus, in one aspect, the present invention provides methods for detecting a target nucleic acid comprising:

(a) providing first and second target-specific nucleic acids, wherein the first and second target-specific nucleic acids each comprise sequences complementary to the target nucleic acid; wherein the first target specific nucleic acid is bound to a first affinity tag and the second target-specific nucleic acid is bound to a second affinity tag, wherein the first affinity tag is capable of binding to a molecular motor, and wherein the second affinity tag is capable of binding to a detection probe;

(b) contacting the first and second target-specific nucleic acids to a sample under conditions whereby the first and second target-specific nucleic acids will hybridize to the target nucleic acid if the target nucleic acid is present in the sample, wherein upon hybridization to the target nucleic acid the first and second target-specific nucleic acids are directly adjacent to each other;

(c) ligating the first and second target-specific nucleic acids together;

(d) binding the molecular motor to the first affinity tag and the detection probe to the second affinity tag;

(e) inducing movement of the molecular motor; and (f) detecting movement of the molecular motor through the detection probe, wherein the movement of the molecular motor serves to detect the target nucleic acid in the sample.

The target nucleic acid can be any nucleic acid that can serve as a bridge between a molecular motor and a detection probe to detect motor-induced motion and for which the means of formation of that bridge is specific to that target nucleic acid. Thus, the target nucleic acid can comprise DNA or RNA and can be single stranded or double stranded. In a preferred embodiment, the target nucleic acid is double stranded. In a more preferred embodiment, the target nucleic acid is a double stranded DNA.

The first and second target specific nucleic acids can be any pair of nucleic acid sequences that are complementary to directly adjacent sequences on the same target nucleic acid. There is no other specific nucleic acid sequence requirement for the first and second target specific nucleic acids. The first and second target specific nucleic acids can independently comprise DNA or RNA and can be single stranded or double stranded. In a preferred embodiment, the first and second target specific nucleic acids are both double stranded. In a more preferred embodiment, the first and second target specific nucleic acids are both double stranded DNA.

As used herein the term "directly adjacent" means juxtaposed 5' phosphate and 3' hydroxyl termini of two adjacent target-specific nucleic acids hybridized to the complementary target nucleic acid, which can be ligated together by the action of a nucleic acid ligase.

The first affinity tag and the second affinity tag may be the same or different as is most suitable for their ultimate attachment to the specific molecular motor and the detection probe employed.

The first affinity tag can bind to the molecular motor and the second affinity tag can bind to the detection probe either directly (for example by a covalent bond between the target-specific nucleic acid and the affinity tag) or indirectly through another molecule. In a preferred embodiment, the first and second affinity tags bind indirectly to the molecular motor and the detection probe, respectively. In this preferred embodiment, the affinity tag binds directly to the target-specific nucleic acid sequence and to an affinity target, wherein the affinity target is bound to the molecular motor or the detection probe. Together, an affinity tag and affinity target make up a binding pair. Either member of a binding pair can be used as an affinity tag and either member can be used as an affinity target. An affinity target includes both separate molecules and portions of molecules, such as an epitope of a protein that interacts specifically with an affinity tag. Antibodies, either member of a receptor/ligand pair, and other molecules with specific binding affinities can be used as affinity tags. Binding an affinity tag to the target-specific nucleic acids thus permits an indirect linkage between the target-specific nucleic acids and the molecular motor or the detection label. An affinity tag that interacts specifically with a particular affinity target is said to be specific for that affinity target. For example, an affinity tag which is an antibody that binds to a particular antigen is said to be specific for that antigen. Complementary nucleotide sequences can be used as binding pairs.

A non-limiting example of a binding pair is biotin/avidin. Other non-limiting binding pair examples include digoxigenin (DIG)/anti-digoxigenin antibody and other antigen/antibody pairs. Epitope tags, such as a his-tag, and antibodies directed against the epitope tag (or fragments thereof) are further examples of binding pairs for use with the methods of the present invention. Those of skill in the art will understand that certain embodiments listed herein as indirect binding of the affinity tag and the molecular motor or detection probe can also be used for direct binding embodiments. For example, where the second affinity tag is an epitope tag as described above, the detection probe can be a labeled antibody against the epitope tag. Many further such examples will be readily apparent to those of skill in the art.

The affinity tags are bound to the first and second target-specific nucleic acids so as to not interfere with the ability of the first and second target-specific nucleic acids to be ligated together after hybridization to the target nucleic acid. In a preferred embodiment, one of the affinity tags is bound at or near the 5' end of one of the target specific nucleic acid sequences, and the other affinity tag is bound at or near the 3' end of the other target-specific nucleic acid sequence, so as to permit juxtaposition of the 5' phosphate and 3' hydroxyl termini of the two adjacent target-specific nucleic acids at the desired site of ligation after hybridization of the target-specific nucleic acids to the target nucleic acid. Such design of the target-specific nucleic acids and the affinity tags is well within the level of skill of those in the art.

The sample in which detection of the target nucleic acid is to be performed can be any sample of interest, including but not limited to synthetic nucleic acids, genomic DNA, cell lysates, tissue homogenates, forensic samples, environmental samples, and isolated nucleic acid samples from cells, tissues, or complete organisms.

Optimization of conditions for contacting the first and second target-specific nucleic acids to a sample under conditions whereby the first and second target-specific nucleic acids will hybridize to the target nucleic acid if the target nucleic acid is present in the sample can be readily accomplished by those of skill in the art. The hybridization conditions are thus optimized to limit hybridization/ligation to those situations where the target nucleic acid is present. Such optimization includes consideration of the nucleic acid probe sequence and length, reaction buffer, reaction temperature, and reaction time. The specific hybridization conditions used will depend on the length of the polynucleotide probes employed, their GC content, as well as various other factors as is well known to those of skill in the art. Non-limiting exemplary conditions can be found at http://www.epicentre.com, by selecting "technical resources-protocols", then accessing "SNP & Mutation Discovery & Screening", then selecting the "Ampliqase Thermostable DNA Ligase" pdf file.

The ligation step of the methods of the invention can be accomplished by techniques known to those of skill in the art using commercially available nucleic acid ligases. Any DNA ligase is suitable for use in the disclosed methods. Preferred ligases are those that preferentially form phosphodiester bonds at nicks in double-stranded DNA. That is, ligases that fail to ligate the free ends of single-stranded DNA at a significant rate are preferred. Thermostable ligases are especially preferred. Many suitable ligases are known, such as T4 DNA ligase (Davis et al., Advanced Bacterial Genetics—A Manual for Genetic Engineering (Cold Spring Harbor Laboratory, Cold Spring Harbor, N.Y., 1980)), *E. coli* DNA ligase (Panasnko et al., J Biol. Chem. 253:4590-4592 (1978)), AMPLIGASE® (Kalin et al., Mutat Res., 283(2):119-123 (1992); Winn-Deen et al., Mol Cell Probes (England) 7(3): 179-186 (1993)), Taq DNA ligase (Barany, Proc. Natl. Acad Sci. USA 88:189-193 (1991), *Thermus thermophilus* DNA ligase (Abbott Laboratories), *Thermus scotoductus* DNA ligase and *Rhodothermus marinus* DNA ligase (Thorbjamardottir et al., Gene 151:177-180 (1995)). T4 DNA ligase is preferred for ligations involving RNA target sequences due to its ability to ligate DNA ends involved in DNA:RNA hybrids (Hsuih et al., Quantitative detection of HCV RNA using novel ligation-dependent polymerase chain reaction, American Association for the Study of Liver Diseases (Chicago, Ill., Nov. 3-7, 1995)).

In a most preferred embodiment, ligation is accomplished by use of a ligation chain reaction. The term "ligation chain reaction" ("LCR") describes the process pioneered by Landegren et al. (1988 Science 241, 1077-1080). This process detects the presence of given DNA sequences based on the ability of two probes to anneal directly adjacent to each other on a complementary target DNA molecule. The two probes are then joined covalently by the action of a DNA ligase, provided that the nucleotides at the junction are correctly base-paired. Thus single nucleotide substitutions can be distinguished. This strategy permits the rapid and standardized identification of gene sequences in genomic DNA, using single molecule FRET as a detection method (M. Wabuyele, H. Farquar, W. Stryjewski et al., *JACS* 125, 6937-6945 (2003)). In this method, the concentration of the solution is controlled so that only one molecule can be present in the volume of the detection cell. Due to its high specificity, LCR can be performed in crude samples, without the need for purifying the nucleic acid target, which significantly simplifies the assay process. The methods of the present invention have as one advantage the ability to detect multiple molecules simultaneously at single molecule detection level. Furthermore, the methods of the invention provide the most sensitive detection method described to date that does not require the use of PCR to amplify the DNA prior to detection, therefore avoiding the many problems inherent in PCR-based nucleic acid detection techniques.

Thus, in a preferred embodiment, the disclosed method uses target dependent DNA ligation reaction (Cheng et al., 1996) to generate a DNA bridge with affinity tags on both ends so that it can serve as a bridge between the molecular motor and the detection probe. Ligation reaction requires the formation of juxtaposed 5' phosphate and 3' hydroxyl termini of the two adjacent target-specific nucleic acids, which are hybridized to a complementary nucleic acid target. The ligation will occur only if the target-specific nucleic acids are perfectly paired to the target nucleic acid and have no gap between them. Therefore, this method is much more specific than hybridization alone and a single-base substitution can be easily detected. In the disclosed methods using double stranded target-specific nucleic acids and target nucleic acid, thousands of copies of the ligated products can be generated from a single copy of target nucleic acid. LCR does not actually copy the target itself. However, after the first pair of target-specific nucleic acids is ligated, double stranded DNA products can be denatured at higher temperature to allow another pair of target-specific nucleic acid probes to hybridize to the same target, followed by further ligation. The process is similar to PCR except the target molecules are not being copied. In this embodiment, thermal cycling is most preferred. In a non-limiting example, conditions employed include an initial hybridization step at 95° C. for two minutes, followed by 19 cycles of 1 minute at 95° C. and 4 minutes at 65° C. in the presence of a thermostable DNA ligase and appropriate reaction components. Those of skill in the art are well-versed in modifying such cycling conditions to provide optimal hybridization and ligation based on the use of different nucleic acid sequences or different buffer conditions.

The molecular motors of the invention include any biological or synthetic molecule capable of induced translational or rotational movements that are capable of detection. In a preferred embodiment, the molecular motor comprises a biomolecular motor. Non-limiting examples of such biomolecular motors comprise $F_1$-ATPases, actomyosin, ciliary axonemes, bacteria flagellar motors, kinesin/microtubules, and nucleic acid helicases and polymerases. In a preferred embodiment, the molecular motor comprises an $F_1$-ATPase.

In some cases the molecular motor may need to be immobilized (i.e. secured in place) for detection. For example, it may be necessary to immobilize the molecular motor for some rotation visualization techniques or if the detection depends on the perturbation of the local environment, such as micro current or impendence. A series of molecular motors, either identical or two or more different molecular motors, can be immobilized on a surface to generate a molecular motor array. If each motor is coated with different affinity targets and different first target-specific nucleic acids (specific to the same or different target nucleic acids) are labeled with different affinity tags, this molecular motor array can be used to detect multiple target nucleic acids in a manner similar to use of a gene chip. As used herein, an "array" comprises a solid surface, with molecular motors attached to said surface. Arrays typically comprise a plurality of molecular motor linked to different capture groups that are coupled to a surface of a substrate in different, known locations. For example, there are several silane derivatives to attach a variety of functional groups to a glass surface. The term "solid surface" as used herein refers to a material having a rigid or semi-rigid surface. Such materials will preferably take the form of chips, plates, slides, cover slips, small beads, pellets, disks or other convenient forms, although other forms may be used. The surfaces are generally coated with an affinity target. Such solid surfaces can be coated in any way that improves desired binding to its surface and/or minimizes non-specific binding to its surface. In a preferred embodiment, nickel-nitrilotriacetic acid (Ni-NTA) affinity resin (Sigma-Aldrich product #P6611) is used. In a further embodiment, acetylated BSA can be added to reduce non-specific binding.

In a preferred embodiment, the first affinity tag attaches to a moiety on the moving component of the motor. By way of example, the rotating subunits on the F1 ATPase include the γ and ε subunits, while the α, β, and δ subunits do not rotate. Thus, where the F1 ATPase is used as the molecular motor, it is preferred that the first affinity tag bind (directly or indirectly) to the γ and/or ε subunits, while the molecular motor is attached via a functional moiety, such as a his-tag, to a substrate through the α, β, or δ subunits. In a preferred embodiment, the $F_1$-ATPase rotary biomolecular motor is a complex of $\alpha_3\beta_3\gamma$ subunits. This complex provides optimal binding of the $F_1$ ATPase to the solid support and the γ subunit to the DNA. Details of F1-ATPase assembly, subunit composition, and inducement of F1-ATPase rotation are well known to those of skill in the art; see, for example, US 20030215844; Yoshida et al., Journal of Biological Chemistry, 252:3480-3485 (1977); Du et al., Journal of Biological Chemistry, 276: 11517-11523 (2001); Bald et al., Journal of Biological Chemistry, 275:12757-12762 (2000); Kato-Yamada et al., Journal of Biological Chemistry, 273:19375-19377 (1998), Kato et al., Journal of Biological Chemistry, 272:24906-24912 (1997); Tucker et al., Journal of Biological Chemistry, 279: 47415-8 (2004); Tucker et al., Eur. J. Biochem. 268:2179-86 (2001), and Du et al., Journal of Biological Chemistry, 276: 11517-23 (2001). Table 1 provides non-limiting examples of F1-ATPase subunits that can be used in the methods and compositions of the present invention.

TABLE 1

GenBank Accession numbers for exemplary ATPase subunits

| | | |
|---|---|---|
| NM_128864 | NM_121348 | NM_104043 |
| D14699 | D14700 | AB095026 |
| BT000409 | AY136289 | AY114540 |
| AJ487471 | M20929 | AF034118 |
| D10491 | X05366 | AY072309 |
| AY062627 | U61392 | U61391 |
| X05970 | AB044942 | AF052955 |
| D37948 | AB022018 | AB007034 |
| D15065 | D00022 | J05397 |
| AF134892 | Z00018 | U46215 |
| X53537 | X03559 | AF010323 |
| AB003549 | D88377 | D88376 |
| D88375 | D88374 | D10660 |
| X68691 | X56008 | X55389 |
| X59066 | L13320 | X51422 |
| Z00026 | X07745 | X55963 |
| X68690 | X56133 | V00312 |
| U37764 | M65129 | J03218 |
| M16222 | J02603 | U09305 |

For example, the "moiety" on the moving component of the molecular motor may be a cysteine residue created by site-directed mutagenesis at a specific position of a protein-based biomolecular motor, such as the γ subunit of F1-ATPase. The first affinity tag can be attached to the cysteine residue through linkage to its sulfhydryl group. Alternatively, an affinity target can be used to coat the molecular motor, and can interact with the affinity tag. This molecular motor coated with affinity targets can then be linked specifically to the affinity tag on the first target-specific nucleic acid. As will be apparent to those of skill in the art, site directed mutagenesis can be used to introduce a cysteine residue (or other useful residues) to various protein-based biomolecular motors so that they can be linked to affinity tags. Furthermore, there are a variety of covalent modification reagents that can modify specific amino acid side chains, as is known to those of skill in the art.

The detection probe can be anything that is capable of attaching to the affinity tag on the second target-specific nucleic acid and providing a means of detecting the movement generated by the molecular motor, such as metallic nanoparticles (rods, spheres, quantum dots, etc.) fluorescent dyes, and nanoparticles labeled with fluorescent dyes. In a preferred embodiment, elemental metal nanorods are used, including but not limited to gold, silver, aluminum, platinum, copper, zinc, and nickel. In one example, gold rod detection probes capable of visual observation by microscope are attached to the second target-specific nucleic acid through a biotin bond. In a further example, the gold nanorod is coated with anti-DIG antibody (the affinity target), which binds specifically to a DIG (Digoxigenin) second affinity tag.

Inducing movement of the molecular motor is done by standard methods in the art for a given molecular motor. For example, the movement of F1 ATPases is induced by adding ATP using standard techniques (Noji, H., Yasuda, R., Yoshida, M. and Kinosita, K. (1997) Nature 386, 299-302). Suitable concentration s of ATP for use in the methods of the invention range from 1 μM to 2 mM; preferably between 200 μM and 1 mM The rate of rotation of the F1-ATPase can be controlled by the ATP concentration used. For example, some detection methods are capable of detecting greater rates of rotation than others (discussed in more detail below), and thus the specific concentration of ATP used will depend in part on the detection technique to be employed.

Those of skill in the art are able to determine how to induce movement of other known molecular motors using similar published protocols. The only motion that will be detected will result from molecular motors that are connected to the detection probe. Since that connection will depend upon the presence of the nucleic acid bridge resulting from specific hybridization of the target specific nucleic acids and the target nucleic acid (and the subsequent ligation), observation of this motion will identify the presence of the target nucleic acid.

Detecting movement of the molecular motor through the detection probe can be accomplished by any suitable means. In one embodiment, direct visualization of the movement is used. In a preferred embodiment, elemental metal rod detection probes capable of visual observation by microscope are attached to the second target-specific nucleic acid. Other means of observation include, but are not limited to single molecule fluorescence resonance energy transfer, fluorescence lifetime anisotropy, and atomic force microscopy. Beside microscopy, other methods can be used to observe the rotation of detection probe, including but not limited to (1) attaching the molecular motor onto a nano-electrode and measure the micro current change or impendence change produced by rotation; (2) attaching a fluorescent label such as Pacific Blue™ (Molecular Probes) on a non-rotating part of the molecular motor; and (3) single molecule anisotropy measurement. In another alternative, rotation can be observed through periodic quenching of the fluorescence signal by a quencher detection probe. In a further alternative, a surface plasmon resonance biosensor can be used to measure the surface plasmon resonance change during metallic nanorod rotation.

In a most preferred embodiment, metal (such as gold) nanorods are used with visible light (400-700 nm wavelength range) to detect the rotation, to provide improved detection capability (See, for example, WO 2004/053501). The light scattered from the nanorods is polarized with the longer and shorter wavelengths scattered from the long and short axes, respectively, of the rod. When viewed through a polarizing filter, the intensity of scattered light depends on the angle of the rod relative to the direction of the filter. The light scattered from the long and short axes of the rod is observed to have a maximum value when those axes are parallel to the direction of the filter and a minimum when perpendicular to the filter. For example, if the long and short wavelengths of scattered light are red and green, respectively, the intensity of the red will be maximum when the green is minimum. Thus, rotation of a metal nanorod viewed through a polarizing filter will appear to blink red and green. In this embodiment, monitoring the oscillation of intensity of both the red and green light as the nanorod rotates provides independent conformation that the rod is rotating. In a further preferred embodiment, the oscillation of intensity of light of only one wavelength is measured, which further improves signal to noise ratios. In these embodiments, measurements can be made using both wavelengths (using, for example, a beamsplitter or a color camera) or just one wavelength of light (using, for example, a green or red filter). Some digital cameras are limited with regard to the frame rate (speed of data collection) at which the camera is still sensitive enough to measure the intensity oscillations from the rotating nanorods. Single photon counters can be used to make the oscillation measurement. The pin hole acts as a camera obscura and the oscillation of only one rod at a time can be measured; it is capable of much greater frame rates at much higher signal to noise. Digital cameras can collect oscillation data on many nanorods at once, while the speed and sensitivity of the camera only needs to be sufficient to capture the rate of rotation of the rod. The preferred oscillation rate is one that is easily measured with the detection device used to make the measurement. In these embodiments employing elemental metal nanorods, dark field microscopy is the preferred detection method, because only the light scattered off the nanorods is observed, further improving signal to noise ratios. In another embodiment, detection is performed using light field microscopy.

Since the methods of the invention are capable of detecting single molecules of a target, they provide a precise means to quantify the amount of target nucleic acid present in a sample. In one embodiment, the number of rotating molecules is determined by visualization and a calculation is made for the fraction of the total sample that is being viewed. This is not possible with fluorescent detection methods in current use with DNA microarrays.

In another aspect, the present invention provides kits for nucleic acid detection comprising first and second target-specific nucleic acids, wherein the first and second target-specific nucleic acids each comprise sequences complementary to a target nucleic acid, wherein upon hybridization to the target nucleic acid the first and second target-specific nucleic acids will be directly adjacent to each other; wherein the first target specific nucleic acid is bound to a first affinity tag and the second target-specific nucleic acid is bound to a second affinity tag, wherein the first affinity tag is capable of binding to a molecular motor, and wherein the second affinity tag is capable of binding to a detection probe. As used in this aspect of the invention, terms carry the same meanings as for previous aspects of the invention.

In preferred embodiments, the kit further contains a molecular motor that binds to the first affinity tag and/or a detection probe that binds to the second affinity tag. In a further embodiment, the molecular motor is bound to a solid support, such as a glass coverslip or other suitable support. The support can be derivatized in any manner suitable for binding to the molecular motor.

The present invention also provides a composition comprising first and second target-specific nucleic acids base-paired with a target nucleic acid and directly adjacent to each other, wherein the first target specific nucleic acid is bound to a first affinity tag capable of binding to a molecular motor and the second target-specific nucleic acid is bound to a second affinity tag capable of binding to a detection probe. In a further embodiment, the first and second target-specific nucleic acid sequences are ligated together.

The present invention also provides a composition comprising:
(a) a nucleic acid complex comprising a first target-specific nucleic acid bound to a first affinity tag capable of binding to a molecular motor; a second target-specific nucleic acid bound to a second affinity tag capable of binding to a detection probe, and a target nucleic acid, wherein the first and second target-specific nucleic acids are base-paired with the target nucleic acid and ligated together;
(b) a molecular motor bound to the first affinity tag; and
(c) a detection probe bound to the second affinity tag.

The present invention further provides a composition comprising:
(a) a solid support; and
(b) a plurality of molecular motors attached to the solid support, wherein the plurality of molecular motors comprise an affinity target for binding to a specific affinity tag.

In a preferred embodiment, the plurality of molecular motors comprises more than one type of molecular motor. In a further preferred embodiment, the different types of molecular motors on the support comprise different affinity targets that are specific for different affinity tags. In a further preferred embodiment, the composition further comprises a first target-specific nucleic acid bound to a first affinity tag that binds to the affinity target on the molecular motor. In a further preferred embodiment, the first target specific nucleic acid is hybridized to a target nucleic acid, and the target nucleic acid is further hybridized to a second target-specific nucleic acid that is bound to a second affinity tag, wherein the second affinity tag is bound to a detection probe.

In a further aspect, the present invention provides methods for gold nanorod synthesis to achieve a higher percentage of nanorods, as described in the examples below. Such methods are of value, since gold nanorods are preferred for use in detection assays, such as those described herein, for the reasons discussed above.

EXAMPLE 1

As shown in FIG. 1A-FIG. 1D, one embodiment of the disclosed methods comprises the following steps:
1. As indicated in FIG. 1A, a first affinity tag is attached to the 5' end of the first target-specific DNA strand. A second affinity tag is attached to the 3' end of second target-specific DNA strand (FIG. 1A).

2. In FIG. 1B the first and second target-specific nucleic acid strands are hybridized to the target nucleic acid so that the 3' end of the first target-specific strand is directly adjacent to the 5' end of the second target-specific strand.

3. In FIG. 1C the first and second target-specific DNA strands are ligated, to generate a double-stranded DNA sequence that contains the first and second affinity tags at each end.

4. In FIG. 1D the double-stranded DNA that contains the affinity tags is then used as a bridge between a molecular motor and the detection probe used to detect the motion generated from the motor via the affinity tags. The first affinity tag attaches specifically to a moiety on a moving component of the molecular motor while the second affinity tag is specific to the detection probe. In the specific preferred and exemplary embodiment the first affinity tag is an avidin link between a moiety on the motor receptor and the first target-specific nucleic acid. The motor shown is the $F_1$-ATPase biomolecular motor. In the specific example, the detection probe comprises gold nanorods that can be visualized by microscopy, attached to the second target-specific nucleic acid by a biotin bond formed. The particular gold rods were of a size and were illuminated such that regularly changing color change from red to green and back, characteristically indicated rotation of the rods.

5. Immobilization occurs after assembly of the components in step 4 (FIG. 2A). Immobilization is effected by histidine binding of the nonrotational F1 motor structure to a nickel surface. 6. The movement of the molecular motor is induced by adding ATP (FIG. 2B). The only motion that will be detected will result from motors that are connected to the attached detection probe. Since that will depend upon the presence of the double-stranded DNA bridge and because the double stranded DNA can only result from the specific hybridization of the three single strands, observation of this motion will identify the presence of the target strand of DNA.

EXAMPLE 2

The following are two examples for detecting multiple target nucleic acids simultaneously:

Approach 1: Detection probes comprising gold rods of different sizes are used to detect ligated DNAs that are specific to pBR322 and Lambda DNA simultaneously using the following procedures:
1. Gold nanorods of different lengths are prepared because the length determines the wavelength of light scattered from it. The short and long gold rods are prepared to enable them to bind to digoxigenin (DIG) and dinitrophenyl-X (DNP-X), respectively.
2. Two pair of target-specific nucleic acids are prepared that are designed to hybridize specifically with pBR322 and Lambda DNA, respectively.
3. To enable the target-specific nucleic acid pairs to bridge between $F_1$ ATPase and a gold nanorod, one target-specific nucleic acid from each pair is labeled with biotin while the other target-specific nucleic acid is labeled with DIG and DNP-X for pBR322 and Lambda DNA, respectively.
4. LCR is performed with the two target-specific nucleic acid pairs.
5. The ligated products are linked to avidin-coated $F_1$ ATPase though biotin/avidin binding.
The assembly is completed upon attachment of the gold nanorods of different lengths.
6. Observation of ATP-dependent rotation of different colored nanorods indicates the presence of the corresponding target.

Approach 2: Ligated DNAs that are specific to pBR322 and Lambda DNA are detected simultaneously on an antibody-coated-$F_1$ ATPase array using the following procedures:
1. $F_1$-ATPase is prepared to enable binding to either anti-DIG antibody and anti-DNP antibody, respectively.
2. Anti-DIG-coated $F_1$ ATPase and anti-DNP-coated $F_1$ ATPase are immobilized on different locations on a cover slip.
3. Two pairs of target-specific nucleic acids are prepared that are designed to hybridize specifically with pBR322 and Lambda DNA, respectively.
4. To enable the target-specific nucleic acid pairs to bridge between $F_1$ ATPase and a gold nanorod, one target-specific nucleic acid of each pair is labeled with biotin while the other target-specific nucleic acid is labeled with DIG and DNP-X for pBR322 and Lambda DNA, respectively.
5. LCR is performed with the two target-specific nucleic acid pairs.
6. The ligated products from pBR322 and Lambda DNA are linked to anti-DIG-coated $F_1$ ATPase anti-DNP-coated $F_1$ ATPase, respectively.
7. The assembly is completed upon attachment of the avidin coated gold nanorods.
8. Observation of ATP-dependent rotation at different location on the cover slip indicates the presence of the corresponding target nucleic acid.

EXAMPLES 3

Four components of a molecular semaphore device were prepared separately: (1) a DNA bridge made from the target DNA; (2) modified F1-ATPase; (3) nickel-coated coverslips; and (4) coated nanorods. After these components were prepared, they were assembled into the device. Rotation of the nanorod attached to the device was observed if the DNA bridge was present to enable assembly of the device.
1. LCR Procedure to Prepare the DNA Bridge.

All oligonucleotides were synthesized by Integrated DNA Technologies (IDT), including those with biotin labels. The target DNA used in this example was F1 plasmid DNA (GenBank accession no. J01594). The two probes used were.

```
5'-CTTGCCGAAGGCATGAAAGTTAAGTG (Probe 1);
and

TACTGGCCGTATCCTGGAAGTTCCG-3' (Probe 2).
```

These sequences are complimentary to the target in the following order:

CTTGCCGAAGGCATGAAAGTTAAGTGTACTGGCCGTATCCTGGAAGTTCCG.

The 5' end of probe 1 contained covalently bound biotin. The 3' end of the probe 2 contained covalently bound DIG or biotin, depending on the experiment.

Template pDNA was prepared using Qiagen's QIAprep Spin Miniprep Kit. Taq DNA ligase and T4 polynucleotide kinase was obtained from New England BioLabs. Thermal cycling was performed with MJ Research PTC-100 thermal cycler. Denaturing PAGE was carried out using BioRad's Mini Protean II system. Catalytic transfer of $P_i$ from the γ position of ATP to the 5'-hydroxyl terminus of the experimental oligonucleotides was achieved using the method entailed in the T4 Polynucleotide Kinase certificate of analysis by New England BioLabs.

Ligation chain reaction was performed according to a procedure reported by Barany (1991, PNAS 88:189-193). 40 units of Taq ligase (New England BioLabs) were added to reaction mixture includes 5 ul 10×Taq ligase buffer, 2.4 μl of each probe (6 μM), 2 μl of various concentration of the target F1 plasmid DNA and 32.4 μl of $H_2O$. LCR was carried out on MJ Research PTC-100 thermal cycler as following: 2 min @ 95° C. and 29 cycles of 1 min @ 95° C. and 7 min @ 65° C. To reduce the detection time, LCR was carried out as described above except the ligation time at 65° C. was decreased. Thus, LCR was accomplished in this experiment within a range of times from 1 to 7 minutes.

LCR at the Presence of Crude Cell Lysate

It was found that DNA bridges could be prepared from target DNA present in crude cell lysate, thereby eliminating the time-consuming DNA purification step. The LCR reaction was carried as described above except that the crude cell lysate from E. coli was used. The DNA bridge was successfully formed from target DNA in the presence of crude lysate from up to 10,000 cells.

Modified F1-ATPase

The F1-ATPase isolated from E. coli strain AB004 contains all five subunits with the stoichiometry $\alpha_3\beta_3\gamma\delta\epsilon$. The sequences of these proteins correspond to gene bank accession numbers: α, AAA24735; β, AAA24737; γ, AAA24736; δ, AAA24734; and ε, AAA24738 with the following changes. Mutations were made to replace all existing cysteines in the α, β, γ, and ε subunits with alanines. The α subunit was mutated to extend the N-terminus with 6 histidines. The γ subunit was mutated to replace lysine-109 with a cysteine that served as the site of biotinylation using biotin maleimide. Biotinylation was carried with a 3-fold molar excess of EZ LINK™ PEO maleimide activated biotin (Pierce Endogen; product #21901) by incubation with gentle shaking for one hour at room temperature. Unbound biotin was removed by size exclusion gel filtration. The biotin covalently bound at this site serves as an effective binding site for avidin, to which the biotinylated DNA is bound via a biotin-avidin interaction. This method is preferred where both ends of the DNA bridge contain biotin.

The placement of this cysteine can be varied on the αβ domain of the γ subunit or on ε subunit to any exposed location that does not interfere with ATPase activity and/or rotation. The three subunit $\alpha_3\beta_3\gamma$ subcomplex of the enzyme can also serve as the F1-ATPase, as can the five subunit F1-ATPase in which the δ subunit cysteines were replaced with alanines by mutagenesis. The 3 subunit or 5 subunit F1-ATPase purified from any biological source will suffice for this task as long as the his-tag and cysteine modifications are made. The his tag used to attach F1 to the coverslip can alternatively (or additionally) be on the α and/or β subunits as long as it does not interfere with ATPase activity. An α3β3γ subcomplex of the F1 ATPase from the thermophilic bacterium PS3 that contained a 10×his tag on the β subunit and a cysteine in a location that facilitated biotinylation and DNA attachment was also used successfully in similar experiments. Similar working construct can also be made using F1, for example, from Chlamydomonas or spinach chloroplasts.

Biotinylated $F_1$ was added to 500 μl of washed nickel-nitrilotriacetic acid (Ni-NTA) affinity resin (Sigma-Aldrich product #P6611), and stirred gently for 30 minutes at room temperature to allow binding of the 6×His-tagged $F_1$ to the Ni-NTA resin. The Ni-NTA resin with bound $F_1$ was loaded into a syringe-column and the column was flushed with 1 ml of a washing buffer. Neutravidin (Molecular Probes product #A2666) was dissolved in wash buffer at a concentration of 1 mg/ml and an approximately 8 to 10-fold molar ratio, relative to the initial $F_1$ concentration, was passed over the Ni-NTA resin to allow binding of Neutravidin to the biotin moieties. Following Neutravidin treatment, the Ni-NTA resin was flushed with 5 ml of washing buffer to remove unbound Neutravidin, then the biotinylated and avidinated $F_1$ was released and collected from the column with 1 ml of an elution buffer. Binding the avidin in this manner to the F1 allows a large excess of avidin to be used and ensures that all the F1 has bound avidin. Any F1 that remains without avidin will decrease the sensitivity of DNA detection. If the avidin is added to the F1 after the F1 has bound to the cover slip, this allows the biotinylated DNA to bind directly to the coverslip in the absence of F1. Such DNA will bind a nanorod but will not be able to rotate, and thus decreases the sensitivity and be counted as increased background.

Following the biotinylation of F1 and gel filtration steps, the recovery of $F_1$ is typically $\geqq 95\%$ of the starting amount. Following binding of biotinylated F1 to Ni-NTA resin, avidination, and elution from the Ni-NTA resin, approximately 75% of the starting $F_1$ was recovered. ATPase activity of biotinylated and avidinated $F_1$ was approximately 90% of the initial activity.

3. Procedure for Preparing Ni-NTA Cover Slip

Ni-NTA cover slips were made following a procedure by Kastner et al. (2003, *Biophysical Journal* 84:1651-1659). The cover glasses (22×22 mm, VWR,) were precleaned by baking at 500° C. for 2 hours. Successively, the glasses were incubated in sealing solution (2% (v/v) 3-glycidyloxypropyl-trimethoxysilane (Fluka, Buchs, Switzerland), 0.01% (v/v) acetic acid) for 3 h at 90° C.; coating solution (2% (w/v) N,Nbis (carboxymethyl)-L-lysine (Fluka, Buchs, Switzerland), 2 mM $KHCO_3$, pH 10.0) for 16 h at 60° C.; and $Ni^{2+}$ solution (10 mM $NiSO_4$, 5 mM glycine, pH 8.0) for at least 2 h at room temperature. After each coating step the glasses were washed with ultrapure water.

4. Protocol to Synthesize Gold Nanorods and Coat them with Avidin.

The factors affecting shape and size of gold nanoparticle include the concentration of cetyltrimethylammonium bromide (CTAB), Au seed concentration, presences of silver ($AgNO_3$), NaOH, ascorbic acid concentration, and appropriate combinations of all these factors. Techniques to increase the percentage of gold nanorods relative to other shapes are of value since gold nanorods are preferred for use in detection assays, such as those described herein. In a typical experiment to synthesize gold nanorods, the CTAB-coated seed solution was prepared by adding 25 µl of Au solution (50 mM) to 10 ml volume of CTAB (100 mM), then 55 µl of NaBH4 (30 mM, ice-cold) was added with strong vortexing for about 2 min. This seed solution can be used immediately, but will keep active at least for one day.

To grow gold nanorods, 100 µl of Au solution (50 mM) was added to 10 ml CTAB (100 mM), followed by adding $AgNO_3$ (10 mM, 50-125 µl) with gentle shaking. Then, 85 µl of ascorbic acid (100 mM) was added with immediate shaking, rendering the solution colorless. Finally, 24 µl of prepared seed solution was added with gentle shaking. A mixture of violet and blue colors appear within 10-20 minutes. Growing gold nanorods at high temperatures (55~100° C.) resulted in more of the deep blue color in the solution. In this method, the seed concentration is the most important parameter for increasing the percentage of nanorods.

Gold Avidination Procedure:
1. 5 ml of gold rod preparation is used;
2. Centrifuge for 10 min at 4000 rpm;
3. Remove supernatant and resuspend pellet in 1 ml of 1 mM CTAB;
4. Centrifuge for 5 min at 6000 rpm;
5. Remove supernatant and resuspend pelled in 0.5 ml of 1 mM CTAB;
6. Take absorbance spectrum;
7. Dilute sample appropriately (with 1 mM CTAB) so that the rod aborbance peak ($A_{650}$) is around 2.0;
8. Add neutravidin to a final concentration of 40 ug/ml;
9. Incubate at room temp with light agitation for 1 hr;
10. Avidinated rods can be stored at room temp or 4 degrees C.

Preparation of Avidin-BSA-C Gold Rods for Rotation Assays:
1. A 1:10 dilution of avidinated rods in Tris buffer (50 mM Tris, 10 mM KCl, pH 8.0) was made;
2. Add BSA-C (acetylated BSA) to a final concentration of 0.1%

The use of BSA-C was found to virtually eliminate the nonspecific binding of the nanorods to the Ni-coated coverslip surface, greatly improving detection sensitivity. It also stabilizes the nanorods so that they do not clump or fall apart.

Although avidin coated gold nanorods were used in this specific example, the nanorods can be coated with any substance that will bind specifically to a specific tag on one end of the DNA bridge. As an example, anti-DIG coated nanorods were prepared by the protocol described below. The anti-DIG coated nanorods were then assembled to the biotinylated F1 with bound avidin, using a DNA bridge that contained biotin at the 5' end and DIG at the 3' end.

Coating of Gold Nanorods with Anti-DIG
Reagents
1. Gold nanorod stock;
2. Anti-DIG (200 µg/ml) in PBS (pH 8.5);
3. 10% BSA in PBS (pH 8.5);
4. 10×PBS (pH 8.5);
5. 1% BSA in PBS (pH 8.5); and
6. 2 mM CTAB Procedure
1. Pipet out 500 µl gold nanorods stock into Eppendorf tube and heat at 37° C. to dissolve all the CTAB.
2. Measure absorbance spectrum in a quartz cuvette from 300 to 900 nm using 10 mM CTAB as the blank (save this and all following spectrum files).
3. Centrifuge the sample at 5,000 rpm (~2,500×g) for 5 minutes.
4. Remove 450 µl of the supernatant, and add 4501 of 2 mM CTAB.
5. Centrifuge again then remove 450 µl of the supernatant.
6. Add another 450 µl of 2 mM CTAB.
7. Measure the absorbance spectrum again using 2 mM CTAB as the blank.
8. To 50 µl of anti-DIG (200 µg/ml), add 500 µl gold nanorods (from the previous steps) rapidly and vortex the mixture.
9. Measure the absorbance spectrum. Blank with 2 mM CTAB.
10. Add 50 µl of 10% BSA in PBS followed by 25 µl of 10×PBS. Vortex briefly.
11. Measure the absorbance spectrum. Blank with 1% BSA, 1 mM CTAB in PBS.
12. Allow the mixture to shake at 4° C. for 30 minutes.
13. Measure the absorbance spectrum. Use the same blank as the previous spectrum.
14. Spot 10 µl onto a glass slide and view under the microscope.
15. Add 16 ul of Anti-DIG and quickly mix by briefly vortexing.
16. Take the absorbance spectrum using the same blank as in Step 5.

17. Allow the mixture to gently shake at RT for 1 hour using the vortexer @ speed 1.
18. Measure the absorbance spectrum using the same blank as previous.
19. Spot 5 µl of the sample onto a slide and allow it to set/dry for ~5-10 minutes. View it under the microscope. Take a picture using the stills camera on the microscope.
20. If the gold nanorods look good (many red spots & minimal aggregation), dialyze them into 20 mM HEPES/2 mM CTAB for 2 hours at RT.
21. After dialysis, measure the absorbance spectrum using the same blank as previous.
22. Store the Anti-DIG coated gold nanorods as +4° C.
5. Assembly of the Components into a Functional Device.
   1. Spot 5 µl of avidinated F1 (80 µg/ml) in Tris buffer (50 µM Tris, 10 mM KCl, pH 8.0) onto a Ni-NTA coverslip;
   2. Incubate 5 min, then wash for 30 sec with Tris buffer;
   3. Add 4 µl biotinylated DNA bridges to the coverslip;
   4. Incubate 5 min, then wash for 30 sec with Tris buffer;
   5. Add 4 µl avidin-BSA-C gold rods to the coverslip;
   6. Incubate 5 min, wash for 30 sec with Tris buffer;
   7. Add 4 µl of Tris buffer to view under the microscope. This will also contain 1 mM $Mg^{2+}$-ATP to induce rotation.

The volume of each of the components added to the coverslip can be varied as desired based on the assay format. Although we have most often added 1 mM $Mg^{2+}$-ATP to induce rotation, we have added as little as 0.4 mM $Mg^{2+}$-ATP and have still observed rotation. At these lower ATP concentrations, the rate of rotation is slower and thus the frame rate needed to record the rotation does not have to be as fast. Rotation may be observed at ATP concentrations as low as 2 µM using the 3 subunit subcomplex of F1 from the thermophilic bacteria PS3. An alternate protocol to assemble the device using the DNA bridge with biotin and DIG such that the DIG would bind to anti-DIG coated nanorods is described below. This experiment also used an F1 that differed from the one described above in that it contained an additional mutation of γY215C for biotinylation, so that avidin can make a two point attachment to F1. This experiment differs from that described above in that it employs a flow cell. Consequently, a movie can be made of the assembled devices before the addition of ATP, then again after ATP is added to induce rotation.

45 µl of 0.5 nM F1 with a subunit composition of $α_3β_3γδε$ and including mutant (γK109C, γL215C) was mixed with 8 µl of 10 µM synthetic DNA bridge (5'biotin CTA ACA TGC TTA GGA TAA TGG CTA ACA TGC TTA GGA TAA TGG DIG 3') (purchased from IDT Technologies, Inc.). The mixture was incubated at room temperature for 30 minutes. An equal volume of BSA (20 mg/ml) was then added to the sample. Microscope flow cells were prepared by attaching an Ni-NTA cover slip to a glass slide using double-sided Scotch tape. Each flow cell was filled with 25 µl of sample and incubated at RT for 5 min. The flow cells were washed with 300 µl washing buffer (50 mM Tris, 10 mM KCl, pH 8) containing 10 mg/ml BSA. 25 µl of anti-DIG coated gold nanorods were added and incubated at RT for 5 min, followed by 5×200 µl washed with washing buffer. 100 µl of rotation buffer (50 mM Tris, 10 mM KCl, pH 8, 0.2 mM ATP, 0.2 mM $MgCl_2$, 29.1 mg/ml phosphoenolpyrivate (PEP), 1.25 mg/ml pyruvate kinase (PK), 1.25 mg/ml lactic dehydrogenase (LDH), 4 mg/ml reduced nicotinamide adenine dinucleotide (NADH)) was added to the flow cell before putting the flow cell under the microscope. The PEP, PK, LDH and NADH were used to regenerate ATP from ADP and phosphate so as to keep the ATP concentration constant throughout the measurement. Movies were taken at 500 frames per second with or without beam splitter. The beam splitter allowed the measurement of the oscillation of the intensity of both the red and green scattered light from the nanorod in each frame of the movie. In the absence of the beam splitter a red filter was used to measure the oscillation of the red only. The analyses of the oscillations are described below.

6. Analysis of the Oscillation of Intensity of Light Scattered from a Nanorod to Determine if it is Rotating.
One-Step Detection Procedure.

Slides are prepared with a fully assembled the molecular semaphore and with ATP present in solution. In order to be able to distinguish Brownian motion from actual rotation, it is preferred to gather data at a rate fast enough to be able to separate the two sources of variation. In a preferred embodiment, this is accomplished using a single photon counter to measure the variation, which permits rotation visualization in real time.
Multistep Procedure Another way that rotation can be detected is to use a flow cell and a high speed video camera. This requires taking at least two movies, although three is preferred. At a minimum, movies are made of a rod in both the presence and absence of ATP. It is helpful to have a movie of the rod while the polarizing lens rotates. This determines the depth of the oscillation of intensity to be expected if that rod is rotating. This control increases the confidence in detecting F1 dependent rotation, however it can be confirmed without the extra measurement.
Software:

Two different software platforms that have been developed to achieve the same goal, is the rod rotating due to the F1 or not. The data collected is always the intensity as a function of time.

The first method involves analyzing trends in the data from the high speed camera. The software reads the data, preferably from three experiments: without ATP, without ATP while rotating the polarizer, and with ATP. The dynamic range expected during rotation is calculated from the polarizer control and can be used to ensure that the molecule being examined is actually a gold rod. The dynamic range is then compared to the standard deviation from the measurements with and without ATP. If the movie with ATP is different than the one without ATP, and fluctuates through the full dynamic range calculated, then the molecule is rotating. The software program is able to do this for all rods in the given field of view. The software is the preferred way of determining rotation, however it is possible to collect and interpret the information by hand to make a final determination. Either way the criteria are the same. The software can be implemented using standard techniques by those of skill in the art. The software is specific to answering the question of whether rotation is occurring or not for all of the rods found in the field of view.

The software developed for the photon counting system calculates numerous statistical measures common in signal processing, including the period, frequency, transition rate, duty cycle, over shoot, under shoot, dwell time, Fourier transformation, and power spectrum. The only required statistic is the power spectrum, although the Fourier transformation is generally calculated to get the power spectrum. From the power spectrum one can determine if there is rotation occurring that is distinct from Brownian motion. It is useful to have the other statistics from additional analysis of the motion, but they are not required to determine if F1 dependent rotation occurs. The software can be implemented using standard techniques by those of skill in the art.

Results:

FIG. 3 provides a summary of experimental results regarding complete assembly vs. nonspecific binding. This graph shows a series of experiments demonstrating that each component of the device must be present for complete assembly. For example, when the biotinlyated DNA bridge is not present, the device cannot fully assemble. These experiments showing incomplete assembly also help to pinpoint the contribution of each component to false positives (due to nonspecific binding). Specifically, it appears that the avidinated gold is not a large source of the nonspecific binding present in the system. The nonspecific binding of avidin and/or DNA directly to the coverslip (which in turn bind gold rods) will result in a low number of false positives which is quantified by this graph. bDNA=DNA bridge biotinylated on both ends, Av=avidin, Au=gold rods, b-dig DNA=DNA bridge biotinylated on one end and dig labeled on the other.

Figure 4:
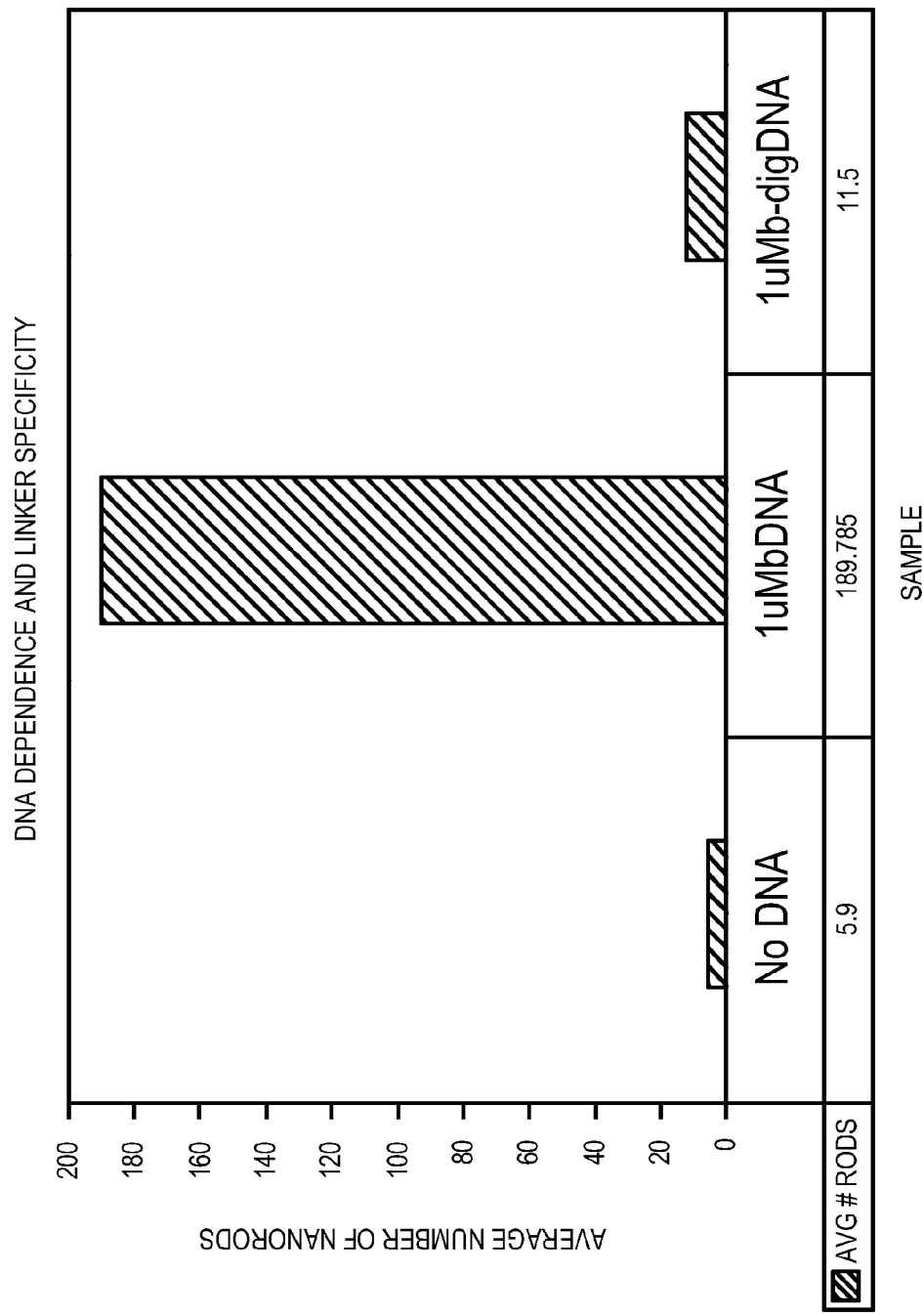
FIG. 4 provides a summary of experimental results regarding DNA dependence and linker specificity.

FIG. 4 provides a summary of experimental results regarding DNA dependence and linker specificity. This graph demonstrates the stringent dependence on the presence of a DNA bridge for device assembly. A DNA bridge was used that was biotinylated on one end and labeled with Digoxigenin on the other end. The biotinylated end of the DNA binds to the avidinated F1 leaving the Dig labeled end free, which is responsible for binding anti-DIG-coated gold rods to complete the device assembly. Since it contains a Dig label, this end of the DNA cannot bind to the avidinated gold rods as shown in the graph. Therefore, this graph shows assembly of the device depends on the presence of a DNA bridge with the correct end labels. According to the data, there is no nonspecific binding of the avidinated gold rods to the DNA backbone (if there was, we would see a higher rod count in the experiment using biotin and Dig labels).

Figure 5:
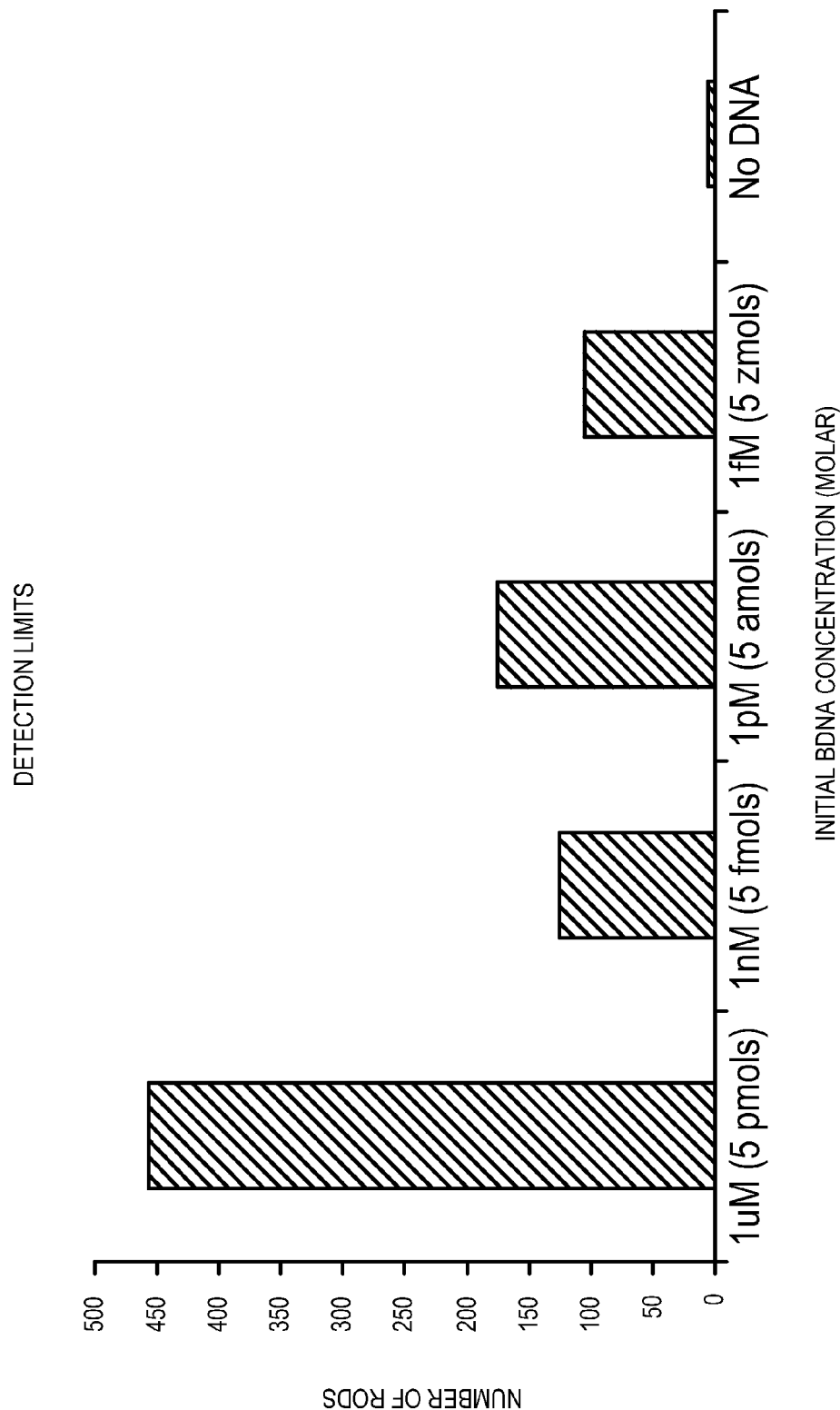
FIG. 5 provides a summary of experimental results regarding detection ability.

FIG. 5 provides a summary of experimental results regarding detection ability. The point of this graph is to show exemplary detection capabilities of biotinylated DNA bridges. Experiments were performed as outlined previously while varying the DNA bridge concentration. Several pictures were taken of the sample area and red spots were counted and summed by a computer program. A concentration dependence on device assembly is seen, as expected. In this figure, 5 gold nanorods were observed to bind nonspecifically to the coverslip. When 300 molecules (5 zmoles) of DNA bridges were added to a coverslip that contained avidinated F1, 103 gold nanorods were observed indicating that about 98 molecules of the DNA bridges were observed (assuming an average of 5 gold nanorods were bound nonspecifically. Thus, this technique allows individual molecules of DNA bridges to be observed. The methods of the invention permit detection of less target DNA, as (1) the background of the method is so low that a significant difference can be detected between assembly at a lower concentration and nonspecific binding, and (2) the use of gold preparations containing nearly 100% gold rods, using the methods outlined above, significantly increases the detection capacity. The detection exemplary capacity ability outlined in FIG. 5 was determined using a gold preparation containing 30% gold rods. Since the detection program used in this example only counts red spots, which are only gold rods, a higher proportion of rods significantly increases the sensitivity level. This suggests that, of the 300 molecules added, almost every one might be counted if the nanorod preparation contained 100% gold rods. As the number of DNA bridges added to the F1-bound coverslip decreases from 300 to about 5 molecules, so that it is within the error of nonspecific binding of the nanorods to the coverslip, the induction of rotation by the addition of ATP will allow the rods attached to F1 via DNA to be distinguished from the rods bound nonspecifically to the surface. In this manner, single molecules of the DNA are detected and quantitated.

FIG. 6A and FIG. 6B provide a summary of experimental results regarding DNA sequence specificity. For any detection method, it is necessary to minimize the number of false positives. DNA detection relies upon the inherent complementary base pairing properties of the molecule. To optimize detection sensitivity, therefore, it is important to minimize the number of DNA bridges formed in the presence of base-pair mismatches between the probes and target molecule. LCR is sensitive to mismatches several bases away from the ligation site. Mismatches prevent ligation form occurring to form the biotinylated DNA bridges. This is represented on the sequence specificity graph, where the number of bridges formed with a mismatched target is dramatically lower than a fully complementary target.

In summary, these graphs demonstrate that the DNA detection method of the present invention can detect the presence of less than 300 molecules of DNA target (fully complementary to the first and second target-specific nucleic acids) without the need to use PCR to amplify the DNA. The DNA bridge only formed when there is a fully complementary target present. The number of molecules of DNA bridge molecules formed can be observed and counted individually when they are assembled with the F1 and the gold nanorod. At the limit at which the gold nanorods stick nonspecifically to the surface, those nanorods that are a component of the semaphore device containing the DNA bridge can be distinguished by the ability of ATP to induce rotation of the nanorod.

REFERENCES

1. Castro, A., T. R. Okinaka, "Ultrasensitive, Direct Detection of a Specific DNA Sequence of *Bacillus anthracis* in Solution," *The Analyst* 125, 9-11 (2000).
2. Castro, A., Williams, J., "Single-Molecule Detection of Specific Nucleic Acid Sequences in Unamplified Genomic DNA," *Analytical Chemistry* 69, 3915-3920 (1997).
3. Castro, A., Shera, E. B., "Single-Molecule Electrophoresis," *Analytical Chemistry* 67, 3181-3186 (1995).
4. Cheng, J., Shoffner, M. A., Mitchelson, K. R., Kricka, L. J., Wilding, P. (1996) Analysis of ligase chain reaction (LCR) products amplified in a silicon chip using entangled solution capillary electrophoresis (ESCE), J. Chromatogr A 732:151-8.
5. Singh-Zocchi, Mukta, Dixit, Sanhita, Ivanor, Vassili, Zocchi, Giovanni (2003) PNAS 100:7605-7610.

We claim:

1. A method for detecting at least one target nucleic acid comprising:
   (a) providing at least one set of first and second target-specific nucleic acids, wherein the at least one set of first and second target-specific nucleic acids each comprise nucleotide sequences complementary to a specific one of the at least one target nucleic acid; wherein each of the at least one set of first and second target-specific nucleic acids are specific only for a selected one of the at least one target nucleic acid; wherein each first target-specific nucleic acid is bound to a selected first affinity tag and each second target-specific nucleic acid is bound to a selected second affinity tag, wherein the selected first affinity tag is capable of binding specifically to a molecular motor, wherein the molecular motor is a biological or synthetic molecule capable of induced translational or rotational movements that are capable of being detected, wherein the selected second affinity tag is capable of binding specifically to a metal nanorod detection probe;
   (b) contacting the at least one set of first and second target-specific nucleic acids to a sample under conditions whereby the at least one set of first and second target-specific nucleic acids will only hybridize to the at least one target nucleic acid if the at least one target nucleic acid is present in the sample, wherein the target nucleic acid and the first and second target-specific nucleic acids' nucleotide-base-pairing-specific-ligation reaction requires formation of juxtaposed 5' phosphate and 3' hydroxyl termini of two adjacent target-specific nucleic acids which are hybridized to the complementary target nucleic acid to form a nucleic acid strand that contains a first affinity tag and a second affinity tag at the 5' and 3' ends respectively;

(c) upon hybridization to the at least one target nucleic acid, ligating the first and second target-specific nucleic acids together;
(d) binding a series of molecular motors on a solid support either before or after assembly with nucleic acid containing affinity tags on the 5' and 3' ends:
(e) binding at least one of the series of molecular motors to the selected first affinity tag;
(f) binding the metal nanorod detection probe to the selected second affinity tag of the molecular motor-target nucleotide complex either before or after the series of molecular motors is bound to the solid support;
(g) inducing translational or rotational movement of at least one of the molecular motors; and
(h) detecting translational or rotational movement of the at least one molecular motor coupled to the solid support as indicated by detecting changes in light intensity of at least one wavelength originating from the metal nanorod detection probe, where the at least one wavelength indicates the presence of a specific target nucleic acid in the sample, or by observing the metal nanorod detection probe translationally moving wherein differing selected colors of each of the translationally moving metal nanorod detection probes indicate the presence of a unique corresponding target nucleic acid in the sample.

2. The method of claim 1 wherein the method further comprises generating a plurality of target and probe nucleotide base-pairing specific ligation products following step (c) using ligation chain reaction.

3. The method of claim 1 wherein the molecular motor comprises F1-ATPase.

4. The method of claim 1 wherein said detecting comprises detecting oscillation of intensity of light of only one wavelength.

5. The method of claim 1 wherein said detecting translational or rotational movement of the at least one molecular motor coupled to the solid support comprises attaching the molecular motor onto a nano-electrode and measuring the micro current change or impendence change produced by rotation.

6. The method of claim 1 further comprising attaching a fluorescent label on a non-rotating part of the molecular motor before detecting translation or rotational movement, where the metal nanorod detection probe is a quencher metal nanorod detection probe, and wherein detecting translational or rotational movement comprises observing rotation through periodic quenching of a fluorescence signal by the quencher metal nanorod detection probe.

7. The method of claim 1 wherein said detecting translational or rotational movement of the at least one molecular motor coupled to the solid support comprises using a detection technique selected from the group consisting of dark field microscopy, single molecule fluorescence resonance energy transfer, fluorescence lifetime anisotropy, atomic force microscopy, single molecule anisotropy measurement, and using a surface plasmon resonance biosensor to measure the surface plasmon resonance change during metallic nanorod rotation.

8. A method for detecting at least one target nucleic acid comprising:
(a) providing at least one set of first and second target-specific nucleic acids, wherein the at least one set of first and second target-specific nucleic acids each comprise nucleotide sequences complementary to a specific one of the at least one target nucleic acid; wherein each of the at least one set of first and second target-specific nucleic acids are specific only for a selected target nucleic acid; wherein each first target specific nucleic acid is bound to a selected first affinity tag and each second target-specific nucleic acid is bound to a selected second affinity tag, wherein the selected first affinity tag is capable of binding specifically to a molecular motor, wherein the molecular motor is a biological or synthetic molecule capable of induced translational or rotational movement that are capable of being detected, wherein the selected second affinity tag is capable of binding specifically to a metal nanorod detection probe;
(b) contacting the at least one set of first and second target-specific nucleic acids to a sample under conditions whereby the at least one set of first and second target-specific nucleic acids will only hybridize to the at least one target nucleic acid if the at least one target nucleic acid is present in the sample, wherein the target nucleic acid and the first and second target-specific nucleic acids' nucleotide-base-pairing-specific-ligation reaction requires formation of juxtaposed 5' phosphate and 3' hydroxyl termini of two adjacent target-specific nucleic acids which are hybridized to the complementary target nucleic acid to form a nucleic acid strand that contains a first affinity tag and a second affinity tag at the 5' and 3' ends respectively;
(c) upon hybridization to the at least one target nucleic acid, ligating the first and second target-specific nucleic acids together;
(d) binding a series of molecular motors on a solid support either before or after assembly with nucleic acid containing affinity tags on the 5' and 3' ends;
(e) binding at least one of the series of molecular motors to the selected first affinity tag;
(f) binding the metal nanorod detection probe to the selected second affinity tag of the molecular motor-target nucleotide complex either before or after the series of molecular motors is bound to the solid support;
(g) inducing translational or rotational movement of at least one of the molecular motors; and
(h) microscopically detecting translational or rotational movement of the at least one molecular motor coupled to the solid support as indicated by detecting changes in light intensity of at least one wavelength originating from the metal nanorod detection probe, where the at least one wavelength indicates the presence of a specific target nucleic acid in the sample, or by observing the metal nanorod detection probe translationally moving wherein differing selected colors of each of the translationally moving metal nanorod detection probes indicate the presence of a unique corresponding target nucleic acid in the sample.

9. The method of claim 8 wherein said microscopically detecting comprises using a microscopy technique selected from the group consisting of dark field microscopy and atomic force microscopy.

10. The method of claim 8 further comprising attaching a fluorescent label on a non-rotating part of the molecular motor before microscopically detecting translation or rotational movement, where the metal nanorod detection probe is a quencher metal nanorod detection probe, and wherein microscopically detecting translational or rotational movement comprises observing rotation through periodic quenching of a fluorescence signal by the quencher metal nanorod detection probe.

* * * * *

SEQUENCE LISTING

<160> NUMBER OF SEQ ID NOS: 4

<210> SEQ ID NO 1
<211> LENGTH: 26
<212> TYPE: DNA
<213> ORGANISM: Artificial sequence
<220> FEATURE:

-continued

```
<223> OTHER INFORMATION: Synthetic oligonucleotide
<220> FEATURE:
<221> NAME/KEY: misc_feature
<222> LOCATION: (1)..(1)
<223> OTHER INFORMATION: 5'-biotin

<400> SEQUENCE: 1
cttgccgaag gcatgaaagt taagtg                                26

<210> SEQ ID NO 2
<211> LENGTH: 25
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (25)..(25)
<223> OTHER INFORMATION: 3'-DIG or 3'-biotin

<400> SEQUENCE: 2
tactggccgt atcctggaag ttccg                                 25

<210> SEQ ID NO 3
<211> LENGTH: 51
<212> TYPE: DNA
<213> ORGANISM: Artificial sequence
<220> FEATURE:
<223> OTHER INFORMATION: Synthetic Oligonucleotide

<400> SEQUENCE: 3
cttgccgaag gcatgaaagt taagtgtact ggccgtatcc tggaagttcc g    51

<210> SEQ ID NO 4
<211> LENGTH: 42
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5'-biotin
<220> FEATURE:
<221> NAME/KEY: misc_feature
<222> LOCATION: (42)..(42)
<223> OTHER INFORMATION: 3'-DIG

<400> SEQUENCE: 4
ctaacatgct taggataatg gctaacatgc ttaggataat gg              42
```